(12) United States Patent
Howell et al.

(10) Patent No.: US 10,425,894 B2
(45) Date of Patent: Sep. 24, 2019

(54) SYSTEM AND METHOD FOR PROVIDING POWER FROM A BATTERY TO A MEDICAL DEVICE

(71) Applicant: Stryker Corporation, Kalamazoo, MI (US)

(72) Inventors: Conner Bacon Howell, Tucson, AZ (US); Sean Christopher Laughery, Vicksburg, MI (US); Michael James Irvine, Byron Center, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 16/009,637

(22) Filed: Jun. 15, 2018

(65) Prior Publication Data

US 2018/0368066 A1 Dec. 20, 2018

Related U.S. Application Data

(60) Provisional application No. 62/520,641, filed on Jun. 16, 2017.

(51) Int. Cl.
| | |
|---|---|
| *H04B 7/00* | (2006.01) |
| *H04W 52/02* | (2009.01) |
| *G06F 1/26* | (2006.01) |
| *H04W 76/10* | (2018.01) |
| *G16H 40/40* | (2018.01) |
| *H04W 12/06* | (2009.01) |

(52) U.S. Cl.
CPC .......... *H04W 52/0225* (2013.01); *G06F 1/26* (2013.01); *G16H 40/40* (2018.01); *H04W 12/06* (2013.01); *H04W 76/10* (2018.02)

(58) Field of Classification Search
CPC ... H04W 4/80; H04W 12/06; H04W 52/0225; H04W 76/10; G06F 1/26
See application file for complete search history.

(56) References Cited

U.S. PATENT DOCUMENTS

| | | | |
|---|---|---|---|
| 6,018,227 | A | 1/2000 | Kumar et al. |
| 6,184,655 | B1 | 2/2001 | Malackowski |

(Continued)

FOREIGN PATENT DOCUMENTS

| | | |
|---|---|---|
| WO | 2007050439 A2 | 5/2007 |
| WO | 2007090025 A1 | 8/2007 |
| WO | 2017112485 A1 | 6/2017 |

*Primary Examiner* — Tuan Pham
(74) *Attorney, Agent, or Firm* — Howard & Howard Attorneys PLLC (57) ABSTRACT

A system and method include a battery removably coupleable to a medical device. The battery includes a cell for storing an electrical charge, a housing, a first contact, and a second contact that is inactive when the battery is not in proximity to the medical device. The battery includes a sensor for generating a proximity signal in response to a proximity of the medical device to the battery that is not based on an electrical connection of the medical device to the contacts. The battery includes a battery controller for receiving the proximity signal, and responsively causing the second contact to be activated. One of the medical device and the battery comprises a communication device. When the medical device is coupled to the battery and the second contact is activated, the communication device transmits an authentication signal to enable authentication.

20 Claims, 7 Drawing Sheets

(56) References Cited

U.S. PATENT DOCUMENTS

| | | |
|---|---|---|
| 7,705,559 B2 | 4/2010 | Powell et al. |
| 8,564,242 B2 | 10/2013 | Hansford et al. |
| 9,219,375 B2 | 12/2015 | Woods |
| 9,780,604 B1 * | 10/2017 | Zeng ........................ H02J 50/10 |
| 2007/0090788 A1 | 4/2007 | Hansford et al. |
| 2015/0182230 A1 | 7/2015 | Belagali et al. |
| 2016/0268647 A1 * | 9/2016 | Umemura ............. H02J 7/0029 |
| 2017/0156710 A1 | 6/2017 | Walton et al. |
| 2018/0076639 A1 * | 3/2018 | Furui ........................ B25F 5/02 |

* cited by examiner

SYSTEM AND METHOD FOR PROVIDING POWER FROM A BATTERY TO A MEDICAL DEVICE

RELATED APPLICATION

The present application claims the benefit of pending U.S. Provisional Patent Application No. 62/520,641, filed on Jun. 16, 2017, the entire disclosure of which is hereby incorporated by reference.

FIELD OF THE DISCLOSURE

This disclosure relates generally to a battery. More particularly, it relates to a battery that is usable to provide power to a medical device. Also described are related systems and methods.

BACKGROUND

A rechargeable battery is capable of repeatedly being charged, storing the charge and delivering the charge to a tool or other device to which the battery is coupled. Rechargeable batteries have, over the years, evolved into reliable power sources for powered surgical tools used in operating rooms to perform surgical procedures. The use of a battery eliminates the need to provide a power cord connected to an external power source. The elimination of the power cord offers benefits over corded surgical tools. Surgical personnel using this type of tool do not have to concern themselves with either sterilizing a cord so that it can be brought into the sterile surgical field surrounding the patient or ensuring that, during surgery, an unsterilized cord is not inadvertently introduced into the surgical field. Moreover, the elimination of the cord results in the like elimination of the physical clutter and field-of-view blockage the cord otherwise brings to a surgical procedure.

A rechargeable battery typically includes a housing and one or more rechargeable cells disposed in the housing. The cells are formed from material capable of storing electrical charge.

Batteries used to power surgical tools are exposed to adverse environmental elements to which batteries used for non-medical uses are seldom exposed. For example, during a surgical procedure, a medical battery may be exposed to blood or other body fluid. Tissue removed from the patient may adhere to the battery. While not an intended part of any procedure, a battery may be exposed to a saline solution. To eliminate the risk of patients being infected during the course of the medical procedure, it is therefore standard practice to sterilize the battery between surgical procedures. This cleaning/sterilization process typically involves rinsing the battery to remove contaminates that are readily visible on the surface of the battery.

Improvements in batteries related to the medical industry are disclosed.

SUMMARY

In one embodiment, a system includes a medical device including a first wireless communication device and a battery removably coupleable to the medical device. The battery includes a cell for storing an electrical charge; a housing; a first contact; a second contact in selective communication with the cell, wherein the second contact is inactive when the battery is not in proximity to the medical device; a sensor disposed within the housing and being configured to generate a proximity signal in response to the medical device and the battery being within a proximity of one another; a second wireless communication device; and a battery controller configured to receive the proximity signal and cause the second contact to be activated in response to receiving the proximity signal, such that when the medical device is coupled to the battery and the second contact is activated, the first wireless communication device transmits an authentication signal to the second wireless communication device to enable authentication.

In another embodiment, a method of authenticating at least one of a battery and a medical device includes steps of providing a battery comprising a battery controller, a contact, and a first wireless communication device; providing a medical device comprising a second wireless communication device and being configured to couple to the contact; sensing a proximity of the medical device to the battery; wirelessly transmitting an authentication signal between the first and second wireless communication devices in response to proximity; and activating the contact in response to the proximity of the medical device to the battery.

BRIEF DESCRIPTION OF THE DRAWINGS

Advantages of the present disclosure will be readily appreciated, as the same becomes better understood by reference to the following detailed description, when considered in connection with the accompanying drawings. Non-limiting and non-exhaustive embodiments of the present disclosure are described with reference to the following figures, wherein like numerals refer to like parts throughout the various views unless otherwise specified.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an examples" means that a particular feature, structure or characteristic described in connection with the embodiment of example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

The present disclosure particularly describes a battery designed to reduce and/or eliminate corrosion of the anode contact when its contacts are exposed to liquids. The battery is further designed so that, when a tool or other medical device is coupled to the battery, initially there is only a minimal drain of the battery's stored charge. Only after the battery determines that the medical device is intended for use with the battery is a continuous charge supplied. If the battery determines that the medical device is not intended for use with the battery, the battery deactivates its terminals to end the supply of charge to the medical device.

The battery includes at least one cell and a battery controller. The battery controller selectively couples the cells to the contacts through which the cells are charged and the cells source charge. In some, but not all embodiments, the battery includes a data contact. Data may be transmitted to and from the battery controller through the data contact. This data may be transmitted to or received from the chargers and medical devices to which the battery is connected.

In other embodiments, the data contact is omitted and data is transmitted from and/or received by the battery with a wireless battery communication device. The data may be received by the battery controller and may be stored in a memory of the battery. In such embodiments, the problem of oxidation of the data contact during sterilization or similar processes is eliminated due to the fact that the data contact has been replaced by a wireless battery communication device. In certain embodiments, the battery is free from a data contact.

When the battery is physically separated from the medical device, the battery may operate in a low power state. When the battery is in the low power state, the battery controller may consume less power than when the battery is in a high power state. In addition, components of the battery, such as the contacts and the battery communication device, may be inactive when the battery is in the low power state. Conversely, when the battery is in the high power state, the components of the battery, such as the contacts and the battery communication device, may be activated and the battery controller may consume more power than in the low power state. In one embodiment, the battery transitions directly to the high power state when the battery exits the low power state, and transitions directly to the low power state from the high power state. Alternatively, the battery may include one or more intermediate power states between the low power state and the high power state. In one embodiment, the battery may include an intermediate authentication power state in which the battery sources an amount of current through the contacts to the medical device that is sufficient to enable the medical device to perform authentication with the battery. In this intermediate authentication power state, the amount of current sourced to the medical device may be lower than the amount of current sourced to the medical device when the battery is in the high power state.

When the battery and the medical device are within a proximity of one another, a sensor within the battery senses the proximity of the medical device and transmits a resulting proximity signal to the battery controller. The battery controller causes the battery to exit the low power state and enter the high power state in response to the signal and couples the cells to the contacts by transmitting a signal to a gating device that selectively couples at least an anode contact to the cells. The medical device may then be electrically coupled to the battery through the battery contacts.

Once the medical device is electrically coupled to the battery through the battery contacts, the medical device receives current from the anode and cathode contacts and activates a medical device communication device. The medical device processor uses the medical device communication device to transmit authentication data including identification information to a battery communication device. The battery receives the identification information and authenticates the medical device if the identification information satisfies the authentication requirement, e.g., the identification information matches a reference identifier. Alternatively, the battery may authenticate the medical device if the identification information includes a serial number, a manufacturer identifier, a cryptographic key, and/or any other suitable data that matches or otherwise corresponds to data stored within the battery memory. If the medical device is authenticated, the battery controller maintains the contacts in an activated state until the battery is removed from the medical device.

In one embodiment, the authentication feature of the battery may allow the battery to source current sufficient for the attached medical device to communicate with the battery. In a further embodiment, the authentication feature of the battery may allow the battery to prevent continued current sourcing to the medical device if the medical device is determined to be not approved for use with the battery. Thus, upon initial coupling of the battery to the medical device, the battery provides a current sufficient for authentication to the medical device. If authentication is successfully completed, the battery may then provide current to the medical device that is sufficient for full operation of the medical device. In one embodiment, the current sufficient for authentication is equal to the current sufficient for full operation of the medical device. In an alternative embodiment, the current sufficient for authentication may be less than the current sufficient for full operation of the medical device.

In one embodiment, authentication data is stored in the battery, rather than in the medical device, since both the battery and the medical device may be subjected to high temperatures (130 degrees centigrade or higher) during an autoclaving process. Specifically, the battery may include a housing and seal that may protect battery components, including the communication device, to a greater degree than the medical device. Accordingly, in this embodiment, the medical device may include a wireless communication device instead of, or in addition to, the wireless communication device of the battery. The medical device may use its wireless communication device to transmit identification data to the battery communication device. The battery controller may store the authentication data within memory of the battery and may authenticate the medical device accordingly. In such a manner, the components of the medical device and the battery may be positioned in an efficient and robust manner to increase a reliability of the medical device and battery by ensuring that only approved or compatible medical devices and batteries are used together.

With the foregoing summary in mind, additional details of the battery are described with reference to FIGS. 1-4. A medical device that may be used with the battery is described with reference to FIG. 2. A charging module that may be used to provide charge to the battery is described with reference to FIGS. 2 and 6. A data structure for storing data relating to the battery is described with reference to FIG. 5. Further details of the method for providing power to a medical device are described with reference to FIG. 7.

Figure 1:
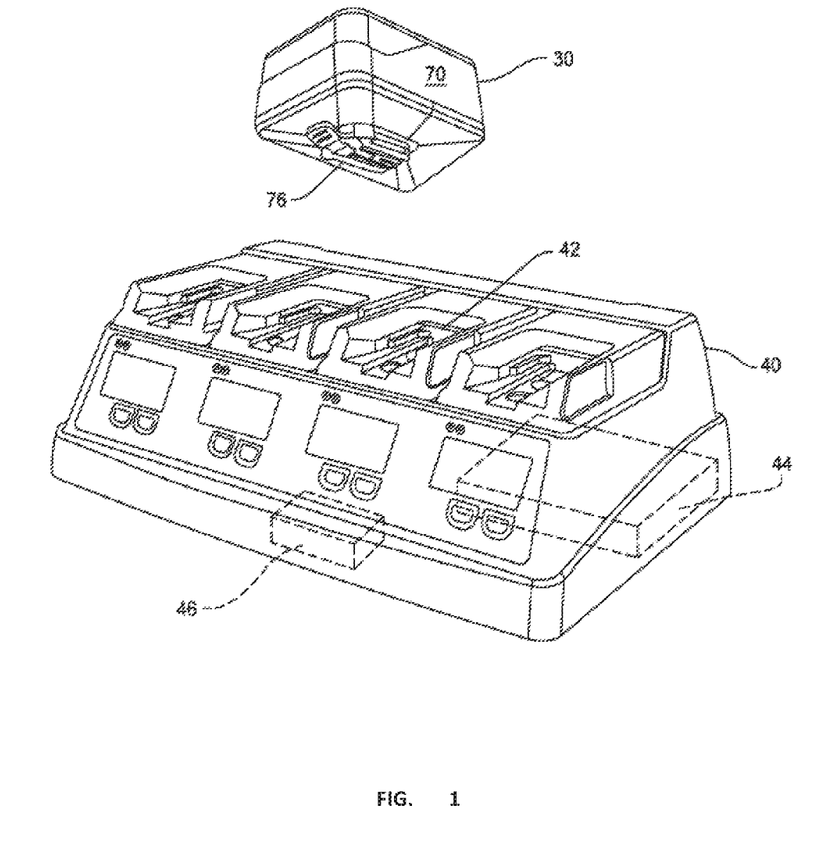
FIG. 1 is a perspective view of a battery and a charger.

FIG. 1 illustrates a battery 30 and a charger 40 according to an example embodiment. Internal to the battery are one or more rechargeable cells (shown in FIG. 3) capable of storing electrical charge. Charger 40 may have at least one socket 42 shaped to releasably hold the battery. Internal to the charger 40 is a power source, illustrated by phantom rectangular block 44. Also internal to the charger is a controller, illustrated by phantom rectangular block 46. When battery 30 is coupled to the charger, the power source 44 applies a charging current to the one or more battery cells 32. Charger controller 46 regulates the charging of the battery by power source 44. The charger controller 46 also is capable of retrieving data from and writing data to memories internal to the battery 30. A further understanding of the charger 40 can be obtained from U.S. Pat. No. 8,564,242, entitled "BATTERY CHARGER CAPABLE OF PERFORMING A FULL OR PARTIAL STATE OF HEALTH EVALUATION OF THE BATTERY BASED ON THE HISTORY OF THE BATTERY", the disclosure of which is incorporated herein by reference.

Figure 2:
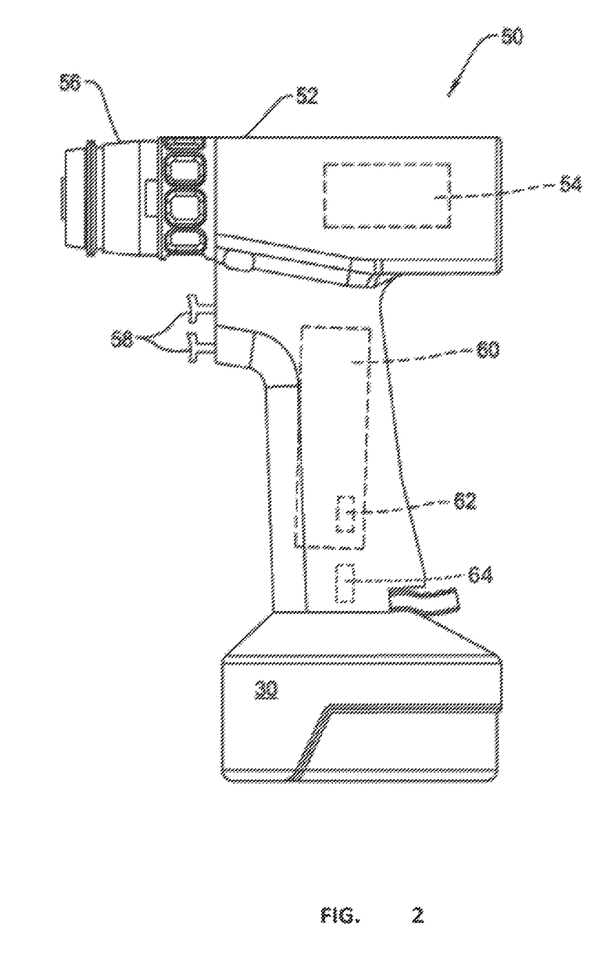
FIG. 2 is a plan view of the battery coupled to a power consuming device.

FIG. 2 illustrates a power consuming medical device 50 coupled to the battery 30. As shown in FIG. 2, the medical device 50 is a powered surgical tool (sometimes referred to as a surgical handpiece) for performing a surgical procedure. In other embodiments, medical device 50 may be a tethered surgical headpiece, or may be any other instrument powered by battery 30 and that is otherwise adapted for use by medical professionals such as, without limitation, lights, cameras, speakers, microphones, sensors, and the like. For the purposes of clarity and consistency, subsequent description of the medical device 50 will generally be made with reference to the powered surgical tool, which is depicted throughout the drawings and which is described in greater detail below. Thus, unless otherwise indicated, the description of the various components and features of the surgical tool described herein also apply to other types of medical devices.

In the illustrated embodiment, tool 50 has a housing 52 that is pistol shaped. The butt end of the tool housing 52 is shaped to releasably receive the battery 30. A powered surgical tool includes a power generating component that converts the electrical energy drawn from the battery cells 32 into another form of energy useful for performing a medical or surgical procedure. In the illustrated embodiment, the power generating component is a motor represented by dashed rectangle 54. Many power surgical tools have a coupling assembly, represented by ring 56. The coupling assembly 56 releasably attaches an energy applicator to the power generating component. The energy applicator is the device that actually applies the energy output by the power generating unit to the target site where the medical procedure is being performed. If the power generating unit is a motor 54, the energy applicator may be what is referred to as a cutting accessory. For simplicity, the tool power generating component is below referred to as motor 54 even though other tools may have other power generating devices that draw current to function.

Alternatively, the tool 50 may have a housing 52 that is pencil shaped as described in U.S. Pub. No. 2015/0182230 entitled "BATTERY AND CONTROL MODULE FOR BOTH ENERGIZING AND CONTROLLING A POWERED SURGICAL TOOL THAT IS RELEASABLY ATTACHED TO THE MODULE", the disclosure of which is hereby incorporated by reference in its entirety. The battery 30 may also share features with the battery described in U.S. Pub. No. 2015/0182230.

Tool 50 also includes at least one manually actuatable control member. The depicted tool 50 has two triggers 58. The triggers 58 are depressed by the practitioner to regulate the actuation of the tool. Also internal to the tool is a control module 60. The control module 60 includes components that monitor the actuation of the triggers 58. Other components internal to the control module, in response to the actuation of the triggers 56, selectively couples the battery cells 32 to the tool motor 52. One of these other components internal to control module 60 is a tool processor 62.

Figure 3:
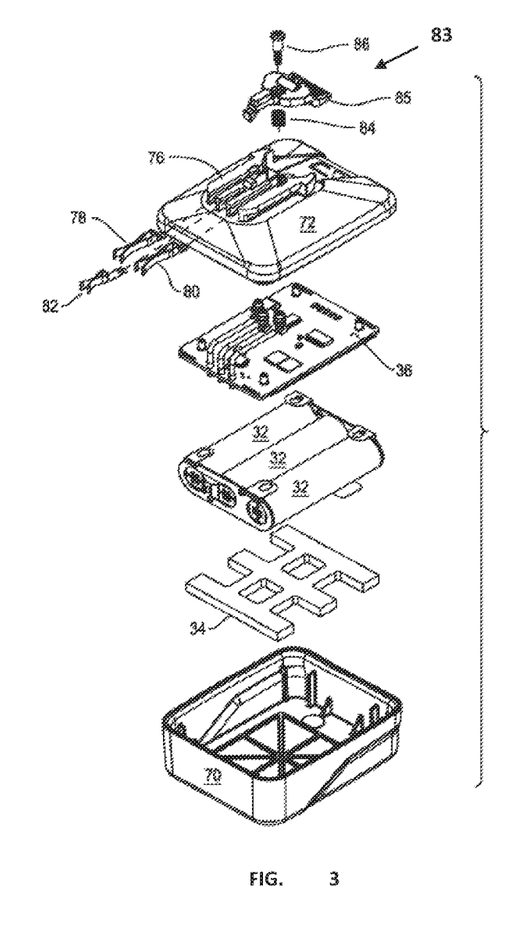
FIG. 3 is an exploded view of the battery.

As seen in FIG. 3, the example battery 30 includes a housing (not labeled in FIG. 3), which includes a shell 70 and a lid 72. The shell 70 includes a plurality of rechargeable cells 32 seated therein. In one embodiment, the cells 32 are connected together in series to form a cell cluster. The cell cluster is seated on a foam pad 34 disposed in the base of shell 70. The lid 72 is sealing disposed over the open top end of the shell 70. If the battery 30 is intended for medical/surgical use, the lid 72 may be coupled to the shell 70 so the shell and lid collectively form a sterilizable housing. Lid 72 is formed with a battery head 76. Battery head 76 is dimensioned to fit both in the charger socket 42 and against the butt end of the tool housing 52 such that the battery head 76 and the housing of the battery 30 may be releasably coupled to either the charger socket 42 or the butt end of the tool housing 52.

Furthermore, as shown in FIG. 3, the battery head 76 is provided with power contacts 78 and 80. Power contacts 78 and 80 are the conductive members through which the charger 40 applies a charging current to the cells 32 and from which the surgical tool 50 draws an energizing current and is provided with an operating voltage. Contact 78 is the cathode and contact 80 is the anode of the battery 30. Furthermore, as shown in FIG. 3, contacts 78 and 80 may be exposed and may be electrically connected to the charger socket 42 or to the medical device via the butt end of the tool housing 52.

Also shown in FIG. 3, in some embodiments, the example battery 30 may include an optional data contact 82. Similar to contacts 78 and 80, data contact 82 may also be exposed and may also be electrically connected to the charger socket 42 or to the medical device via the butt end of the tool housing 52. However, in embodiments including the data contact 82, the data contact 82 does not provide an operating voltage, but instead provides data and instruction signals, which are written into and read out from the battery 30 through data contact 82. The battery 30 may thus use the data contact 82 to exchange data and instructions with charger controller 46, tool processor 62, and processors of the modules. These signals may be exchanged between the various processors using a one-wire signal exchange protocol. One such protocol is the Dallas Semiconductor One-Wire protocol. However, it should be noted that, in other embodiments, data contact 82 may be omitted, and data and instructions may be written into and read out from battery 30 using a wireless communication device (described more fully herein). Accordingly, the battery 30 is free of a data contact.

The battery 30 and/or tool 50 may optionally include a latching system 83 to secure the battery to the tool. The latching system 83 may include a latch 85. The latch 85 may be pivotally mounted to the battery lid 72. The latch 85 holds the battery 30 to the butt end of tool housing 52. A pin 86 holds latch to the lid 72. A spring 84 biases one portion of the latch away from the adjacent surface of the lid 72.

Mounted to the cell cluster so as to be disposed between the cells 32 and lid 72 is a circuit board 36. Circuit board 36 holds the below described components that selectively connect cells 32 to the anode contact 80 and the cathode contact 78.

In example embodiments, cells 32 are lithium ion cells. For example, cells 32 may include any suitable nickel or lithium chemistry cell, including but not limited to, lithium ion ceramic cells, lithium iron phosphorous oxynitride cells, or lithium tin phosphorous sulfide cells. One such cell is the APR18650MIA cell manufactured by A123 Systems of Waltham, Mass. In alternative embodiments, cells 32 may be lead acid, or any other suitable type of cell. Each cell, when properly charged, has a nominal cell voltage of 3.3 VDC. In many, but not all embodiments, the cells are connected together in series. In the illustrated embodiment, battery 30 includes 3 series connected cells 32. This version of battery 30 is therefore configured to output a charge at a potential of around 9.9 VDC. Alternatively, in some embodiments, at least some of the battery cells may be connected together in parallel.

The physical structure of the battery may also be different from what is described and illustrated. For example one or more of the contacts 78 and 80 may be mounted directly to the housing as opposed to the lid 72. Likewise the circuit board 36 that holds the electrical components internal to the battery 30 may be mounted to the housing or lid 72 instead of being mounted to the cell cluster.

Figure 4:
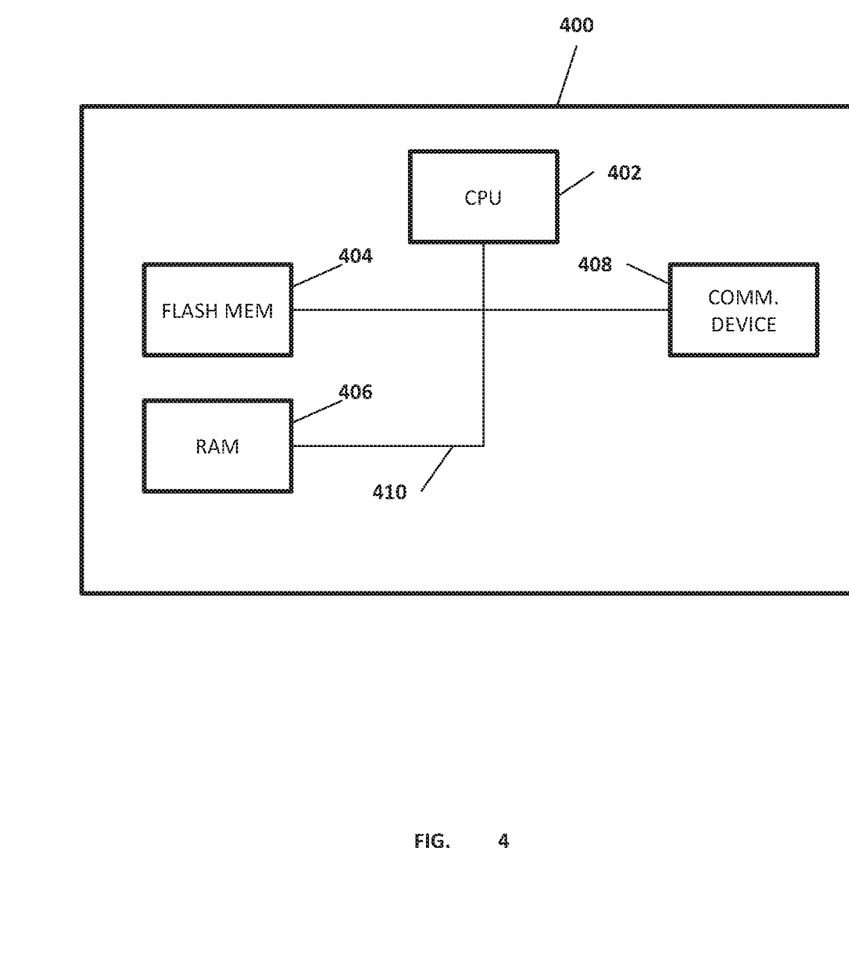
FIG. 4 is a block diagram of an example controller that may be included within the battery.

FIG. 4 is a block diagram of an example controller 400 that may be included within battery 30 to control the operation of battery 30, as described more fully herein.

In an example embodiment, controller 400 includes a central processing unit (CPU) 402 for controlling the operation of controller 400 and the components connected to the controller. A non-volatile flash memory 404 stores instructions executed by the CPU 402. As described more fully herein, memory 404 also stores the instructions used to regulate the charging of the battery 30, data describing the use history of the battery 30, and data describing the use history of the tool 50 to which the battery 30 is coupled. A random access memory 406 functions as a temporary buffer for data read and generated by controller 400.

Battery controller 400 may also include a wireless or wired communication device 408. This communication device 408 may be a radio frequency (RF) or infrared (IR) transceiver. In some versions, the communication device 408 may be a Bluetooth transceiver. When the battery is connected to the tool, communication device 408 exchanges signals with a complementary transceiver within tool 50 (or within another suitable medical device).

In FIG. 4, the above sub-circuits are shown interconnected by a single bus 410. It should be appreciated that this is for simplicity. In practice, dedicated lines may connect certain of the sub circuits together. Likewise it should be understood controller 400 may have other sub-circuits. These sub-circuits are not described in detailed.

Figure 5:
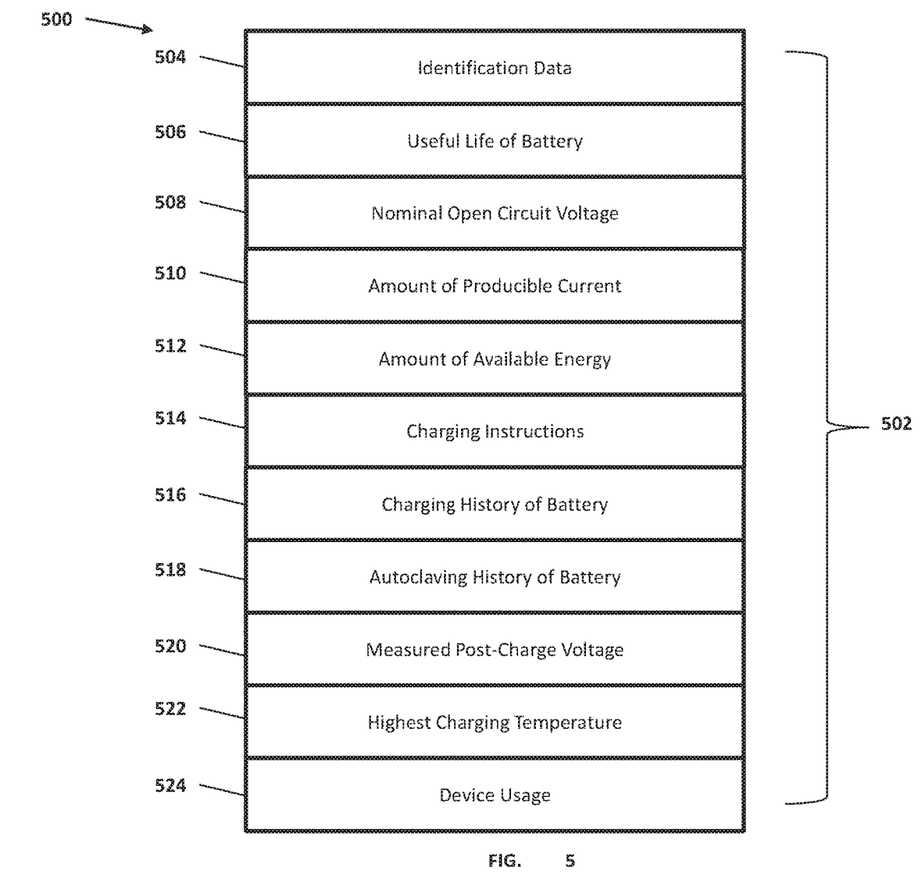
FIG. 5 is a block diagram of an example data structure that may be stored in a memory of the battery controller.

FIG. 5 is a block diagram of a data structure 500 that may be stored in flash memory 404 (shown in FIG. 4) in addition to the instructions executed by the controller 400. The data structure 500 may store data as one or more fields 502 in one or more records or files. As one example, identification data 504 may be stored in the file and may be used to identify the battery. The identification data 504 may include, for example, a serial number, a lot number, a manufacturer identification, and/or an authorization code. The authorization code or other identification information may be read by the tool 50 or charger 40 to which the battery is connected to authenticate the battery (e.g., to determine if, respectively the battery can power the tool or be recharged by the charger). The flash memory 404 may also include a field indicating the useful life 506 of the battery (sometimes referred to as "useful life data"). Useful life data may include one or more of the following data types: battery expiration data, a number of charging cycles that the battery has undergone, and a number of autoclaving procedures or cycles the battery has been subjected to. Other fields may indicate the nominal open circuit voltage 508 of the signal produced by the battery, the current 510 the battery can produce, and the amount of available energy 512 (represented in joules, for example).

Charging instructions 514 for the battery may be stored in a field. This data can include the types of data described in the memories of the batteries disclosed in U.S. Pat. Nos. 6,018,227 and 6,184,655, the disclosures of which are hereby incorporated by reference.

Flash memory 404 also contains data describing a charging history 516 and autoclave history 518 of the battery. For example, as part of the charging history 516 of the battery 30, data may be stored indicating the number of times the battery was charged as well as a timestamp indicating the time each charging cycle was initiated and/or ended.

As part of the autoclaving history 518 of battery 30, flash memory 404 may store data indicating the total number of times the battery has been autoclaved, and a cumulative amount of time the battery 30 has been subjected to temperatures at or above a threshold considered to be the autoclave temperature. In one embodiment, the threshold temperature is about 130 degrees centigrade. In a more specific embodiment, the threshold temperature is about 134 degrees centigrade. The autoclaving history 518 field may also include data indicating the number of times and/or the cumulative amount of time the battery has been exposed to potentially excessive autoclaving cycles. The autoclaving history 518 may also include peak autoclave temperature data indicating the highest autoclave temperature to which the battery 30 has been exposed and an amount of time the battery 30 has been in an autoclave for each of its autoclaving cycles, as well as a period of the longest single time the battery was subjected to autoclaving.

A measured post-charge voltages field 520 contains data indicating the measured voltages-at-load of the battery after each charging. In some embodiments, field 520 only contains these measurements for the last 1 to 10 charging cycles. In another field 522, data is stored indicating the highest battery temperature measured during its previous charging cycles. Again, field 522 may only contain data indicating the highest temperatures measured during the last 1 to 10 charging cycles of the battery.

Flash memory 404 also contains a medical device history field 524. As discussed below, medical device history field 524 stores data obtained from the tool 50 or other medical device that battery 30 is employed to power. For example, in one embodiment, medical device history field 524 may store data indicating a number of times that the battery 30 has been connected to tool 50, a number of trigger pulls of tool 50, a total amount of time that the battery has provided power to tool 50 during an operation of tool 50, a number of power cycles that tool 50 has undergone, and/or any other suitable data of tool 50. The data stored in medical device history field 524 may be transmitted by a communication device of tool 50 and received by a communication device of battery 30.

Figure 6:
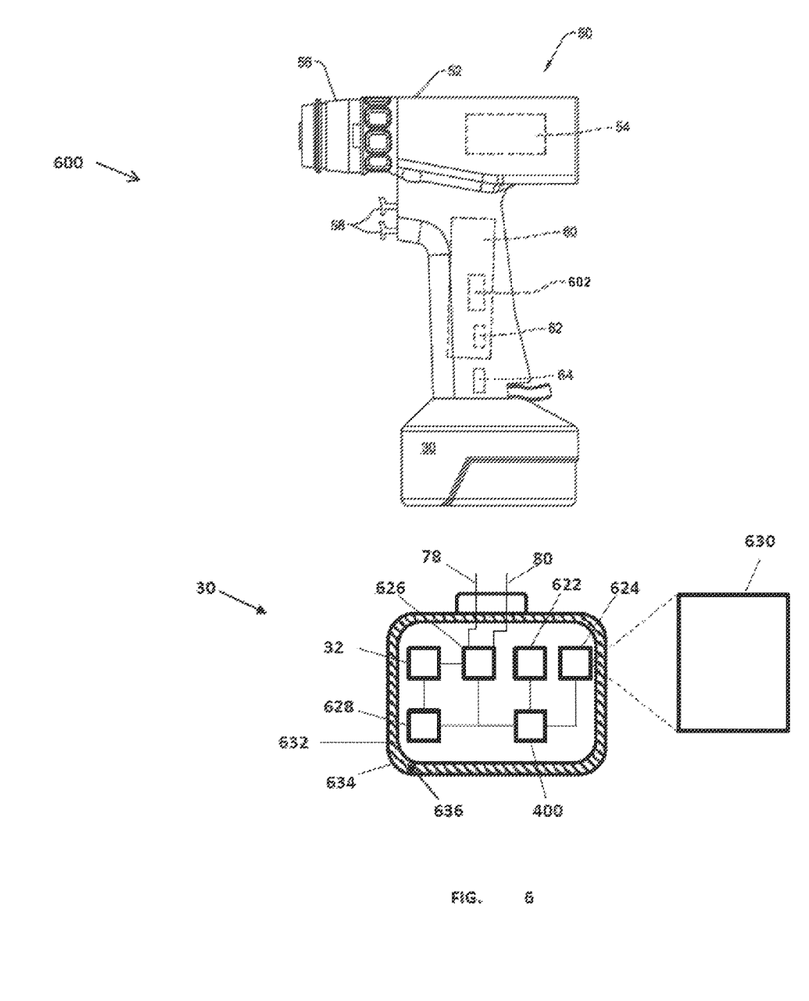
FIG. 6 is a block diagram of a system including a medical device and a battery.

FIG. 6 is a block diagram of a system 600 including a medical device and a battery 30. In the embodiment shown in FIG. 6, the medical device is a hand-held motorized surgical tool 50 that may be used to impart energy to a portion of a patient's anatomy. For example, the medical device may be a motorized bur, saw, or drill that may be used to cut or remove tissue from a target site in the patient's anatomy. Alternatively, the medical device may be a surgical helmet or headpiece as described in PCT Application Serial No. PCT/US16/66633 entitled "HEAD UNIT SYSTEM WITH CONNECTOR FOR PERIPHERAL DEVICE", the disclosure of which is hereby incorporated by reference in its entirety, or any other suitable device. The following embodiments will be described with the medical device being tool 50, with the understanding that the medical device is not thus limited.

As illustrated in FIG. 6, battery 30 may be electrically disconnected from, and spaced apart from, tool 50 while battery 30 is being charged, sterilized, etc. When battery 30 is disconnected from tool 50, tool 50 is in an unpowered state since tool 50 does not receive power from battery 30. In a similar manner, battery 30 may enter a low power state when battery 30 is disconnected from tool 50. Battery 30 may enter the low power state immediately after being disconnected from tool 50 or may enter the low power state when a predetermined amount of time elapses after being disconnected from tool 50. If battery 30 detects that the tool 50 is in proximity to the battery 30, the battery may exit the low power state and enter the high power state as described more fully herein. Battery 30 may exit the low power state and enter the high power state immediately after determining that tool 50 is in proximity to battery 30, when a proximity signal exceeds a predetermined threshold, or after a predetermined amount of time elapses after the battery determines that tool 50 is in proximity to battery 30. In various embodiments, the predetermined amount of time may vary. For example, the predetermined amount of time may be 5 seconds, 10 seconds, 15 seconds, or another other suitable amount of time. In other embodiments, the predetermined amount of time may be based on a time used for authenticating the tool 50 and/or battery 30 after the tool 50 is in proximity to battery 30.

In one embodiment, tool 50 includes a communication device 602 as well as housing 52, motor 54, ring 56, triggers 58, control module 60, and tool processor 62 as described above. Further, as illustrated in FIG. 6, battery 30 includes a plurality of components including controller 400 (described above), a proximity sensor 622, one or more cells 32, a battery communication device 624, a gating device 626, and a charging circuit 628. The battery components described herein may be included within a circuit board, such as circuit board 36 (shown in FIG. 3).

Tool communication device 602 is a device that enables tool 50 to communicate with other devices including, but not limited to, battery 30. In one embodiment, tool communication device 602 communicates bi-directionally with battery communication device 624 to transmit authentication data, usage data, and/or any other suitable data as desired. Tool communication device 602 may be a wireless communication device that communicates with battery communication device 624 using a suitable wireless protocol such as Bluetooth, Wi-Fi, or NFC, or may be a wired communication device that communicates with battery communication device 624 via a contact of battery 30 (e.g., data contact 82). Alternatively, communication device 602 may be a combined device that communicates with battery communication device 624 by both wireless and wired mechanisms.

Referring to the components of battery 30, proximity sensor 622 is configured to sense a proximity of tool 50 and to generate a signal in response to the proximity of tool 50. Sensor 622 may be a magnetic sensor (e.g., a Hall effect sensor), a contact sensor, an antenna attuned to receive RF signals such as near-field communication (NFC) signals, radio frequency identification (RFID) signals, or any other suitable sensor. Sensor 622 generates a proximity signal that is associated with a distance or proximity of tool 50 to battery 30. Accordingly, in one embodiment, an amplitude of the proximity signal may increase as tool 50 moves closer to battery 30, and the amplitude of the proximity signal may decrease as tool 50 moves away from battery 30. Alternatively, the amplitude of the proximity signal may be fixed and may selectively be generated when sensor 622 senses the proximity of tool 50 to battery 30. Sensor 622 transmits the proximity signal to battery controller 400 to enable controller 400 to detect the proximity of the tool 50 with respect to battery 30.

In an embodiment in which sensor 622 is a magnetic sensor, sensor 622 may generate the proximity signal when a magnet coupled to, or is disposed within, tool 50 generates a magnetic field that is sensed by sensor 622. For example, the tool 50 may include a magnet 64, as shown in FIGS. 2 and 6, which generates a magnetic field. Accordingly, sensor 622 may sense the magnetic field and generate the proximity signal accordingly. In one such embodiment, the sensor 622 may include a Hall effect for sensing the magnetic field. Furthermore, in such an embodiment, the magnet 64 and the sensor 622 may be positioned such that the sensor 622 senses the magnetic field when the medical device and the battery 30 are brought within the proximity of one another. For example, in an embodiment where the tool 50 includes the latching system 83, the latching system may include the magnet 64 such that when the latching system 83 is being coupled to the housing of the battery 30, the sensor 622 senses the changing magnetic field.

In another embodiment, sensor 622 may be a contact sensor that is actuated by the physical connection of tool 50 to battery 30. For example, the contact sensor may be a physical, electrical, or magnetic switch that is activated by the physical connection of tool 50 to battery 30.

Cells 32 are used for storing charge within battery 30. In one embodiment, the cells may be high-temperature cells configured to sustain functionality without damage or with reduced damage during sterilization (e.g., during an autoclave process). The cells may include thermal insulation to minimize damage incurred during sterilization or autoclave cycles. The thermal insulation may comprise an aerogel, such as polyimide, silica, or carbon aerogel. The number and type of cells internal to the battery may of course be different from what is described.

Battery communication device 624 may be a transceiver (e.g., communication device 408) that allows controller 400 to connect to tool 50, charger, module, and/or a computing device, such as a tablet or server. In an embodiment in which battery communication device 624 is a wireless transceiver, battery communication device 624 may wirelessly transmit and receive data using any suitable wireless protocol and/or technology, including but not limited to, ZigBee, Bluetooth, Wi-Fi, etc. Alternatively, battery communication device 624 may be a wired transceiver that transmits data to and from tool 50 and/or a computing device using a suitable wired protocol, such as the Dallas Semiconductor One-Wire protocol or the like. A user may send and/or receive data from battery 30 and/or tool 50 using battery communication device 624.

As described more fully herein, battery communication device 624 may transmit authentication data to tool communication device 602 and/or may receive authentication data from tool communication device 602 to authenticate tool 50 and/or battery 30. Accordingly, battery 30 and/or tool 50 may ensure that only authorized or compatible components are being used with each other.

One implementation of battery communication device 624 is an NFC or RFID tag that includes an integrated tag memory 630 for storing authentication data. For example, tag memory 630 may include a unique identifier for battery 30, such as a device identifier, a serial number, etc. Additionally or alternatively, tag memory 630 may include other identification information, including an identifier for the manufacturer of battery 30, an access code, or the like. Battery communication device 624 may transmit the identification information to tool 50 during authentication. Alternatively or additionally, tool 50 may transmit identification information of tool 50, such as a device identifier, a serial number, a manufacturer identifier, an access code, etc., and battery communication device 624 may store the tool's identification information in tag memory 630 or another suitable memory. In an alternative embodiment, tag memory 630 is a portion of flash memory 404.

Gating device 626 includes one or more circuit components that selectably couple cells 32 to contacts 78 and 80. In one embodiment, gating device 626 includes one or more transistors, such as field effect transistors, that are activatable by battery controller 400 to electrically couple cells 32 to contacts 78 and 80 such that cells 32 are selectively in communication with cathode contact 78 and anode contact 80. Alternatively, gating device 626 may include any other suitable transistor, switch, or other device that enables cells 32 to be selectably coupled to contacts 78 and 80.

Charging circuit 628 includes one or more circuit components that facilitate charging, or providing charge or current to, cells 32. In one embodiment, when battery 30 is coupled to a charging device, current is received from the charging device through cathode contact 78 at one or more voltages. Charging circuit 628 may receive the current and may adjust the current and/or voltage to conform to a desired current or voltage of cells 32. When the cells 32 have been charged to a maximum or predetermined state of charge, charging circuit 628 may prevent further current from being provided to cells 32.

The various components of battery 30 may be positioned within a housing 632. The housing 632 may include a cover 634 that may be welded to the housing 632 to form a unitary structure to form a seamless bond. In addition, a seal 636 may be positioned between housing 632 and cover 634 to form a hermetic barrier between cover 634 and housing 632. Seal 636 may be formed of a material that is sterilizable and, optionally, compressible. For example, seal 636 may comprise EPDM rubber or silicon rubber.

Contacts 78 and 80 are mounted to cover 634. While contacts 78 and 80 are illustrated in FIG. 6 as extending from cover 634 and exposed, it should be recognized that contacts 78 and 80 may be partially or completely housed within cover 634 and/or housing 632 such that a corresponding contact from tool 50 inserts into cover 634 and/or housing 632 to connect to contact 78 and contact 80. Contact 78 is sometimes referred to as a cathode contact. Contact 80 is sometimes referred to as an anode contact. Contacts 78 and 80 (and cover 634) are shaped and physically adapted to enable battery 30 to removably couple to tool 50. More specifically, contacts 78 and 80 are physically adapted to be inserted into a corresponding portion of tool 50 to establish physical and electrical connection with tool 50. Thus, when cathode contact 78 and anode contact 80 are inserted into tool 50 and contacts 78 and 80 are activated such that a voltage is applied across anode contact 80 and cathode contact 78, battery 30 provides power to tool 50.

The housing 632 of the battery may comprise a material suitable for autoclave cycles, including, but not limited to, polyether ether ketone, polyetherimide, polyphenylsulfone, etc. The battery assembly, including the battery components, housing 632, and cover 634, is configured to be sterilized, together or separate from the tool, via steam sterilization, hydrogen peroxide sterilization, or other suitable sterilization technique. By "sterile," it is meant that, once the process is complete, the housing 632 or cover 634 has a sterilization assurance level (SAL) of at least $10^{-6}$. This means that there is equal to or less than one chance in a million that a single viable microorganism is present on the sterilized item. This definition of sterile is the definition set forth in the ANSI/AAMI ST35-1966, entitled "Safe Handling and Biological Decontamination of Medical Devices in Health Care Facilities and Nonclinical Settings". For alternative applications, the "sterilization" process is sufficient if, once the process is complete, the housing 632 or cover 634 has an SAL of at least $10^{-4}$.

Also while many versions of the battery include a housing 632 or cover 634 that is sterilizable, that need not always be the case. This feature is often not part of the design for a battery of that is not designed for medical/surgical use. Likewise, the features of this battery may be incorporated into what is often referred to as aseptic battery. An aseptic battery includes a cell cluster and a circuit board to which the electrical components such as the cell regulator (voltage regulator), the transistors (e.g., FETS), the resistors, capacitors, and microprocessor or controller are monitored. This cell cluster is not sterilizable. Instead, the cell cluster can be removably fitted into a housing that is sterilizable. Once the cell is fitted in the housing, the housing is sealed. The cells and other cluster-forming components are thus encapsulated in a sterilized enclosure. Contacts integral with both the cell cluster and the housing provide the contact path over which current is sourced from the battery. A further understanding of the structure of an aseptic battery assembly can be obtained from U.S. Pat. No. 7,705,559, entitled "ASEPTIC BATTERY WITH A REMOVAL CELL CLUSTER, THE CELL CLUSTER CONFIGURED FOR CHARGING IN A SOCKET THAT RECEIVES A STERILIZABLE BATTERY" and PCT Pub. No. WO 2007/090025 A1, entitled "ASEPTIC BATTERY ASSEMBLY WITH REMOVABLE, RECHARGEABLE BATTERY PACK, THE BATTERY PACK ADAPTED TO BE USED WITH A CONVENTIONAL CHARGER", the disclosures of which are incorporated herein by reference.

Some batteries are also provided with supplemental components. These components may include internal sensors, data collection circuits, memories or control processors. These components may monitor the environment to which the battery is exposed, store data regarding the use of the battery, and/or store data regarding the medical device to which the battery is coupled. The supplemental components may include or be similar to the supplemental components described in U.S. Pat. No. 6,018,227, entitled "BATTERY CHARGER ESPECIALLY USEFUL WITH STERILIZABLE RECHARGEABLE BATTERY PACKS", U.S. Pat. Pub. No. 2007/0090788/PCT Pub. No. WO 2007/050439 A2, entitled "SYSTEM AND METHOD FOR RECHARGING A BATTERY EXPOSED TO A HARSH ENVIRONMENT", and U.S. Pat. No. 9,219,375, entitled, "BATTERY CAPABLE OF WITHSTANDING THE EFFECTS OF LIQUID SUBMERSION", the disclosures of which are incorporated herein by reference. When a battery is provided with one or more of these supplemental components, the battery housing may include a supplemental contact (e.g., data contact 82). This supplemental contact may be the contact through which signals are received from and/or transmitted to the supplemental components.

During any one of the above events, a liquid bridge can form between the cathode and anode contacts. These liquids, even if just tap water, can form a conductive bridge between the cathode and the anode. If the bridge is conductive, there is current flow between the contacts. The conductive liquid undergoes an electrolytic reaction with the metal forming the anode contact. As a consequence of this reaction, a layer of metal oxide forms on the anode contact. This oxide layer functions as an impedance layer. The presence of this impedance layer reduces the efficiency of the both the charging of the battery and of the battery to deliver charge to the tool to which the battery is coupled.

If the battery is provided with supplemental components that use a data contact for transmission or receipt of data, the exposure of the battery contacts to liquid may also cause oxidation of the data contact. The resultant oxide layer, if of sufficient size/thickness, may essentially function as a resistor in series with the data contact. The presence of this oxide layer can attenuate the levels of the signals applied to or read out from the battery over the data contact. This voltage attenuation may be such that signals cannot be processed by the components to which they are applied.

Figure 7:
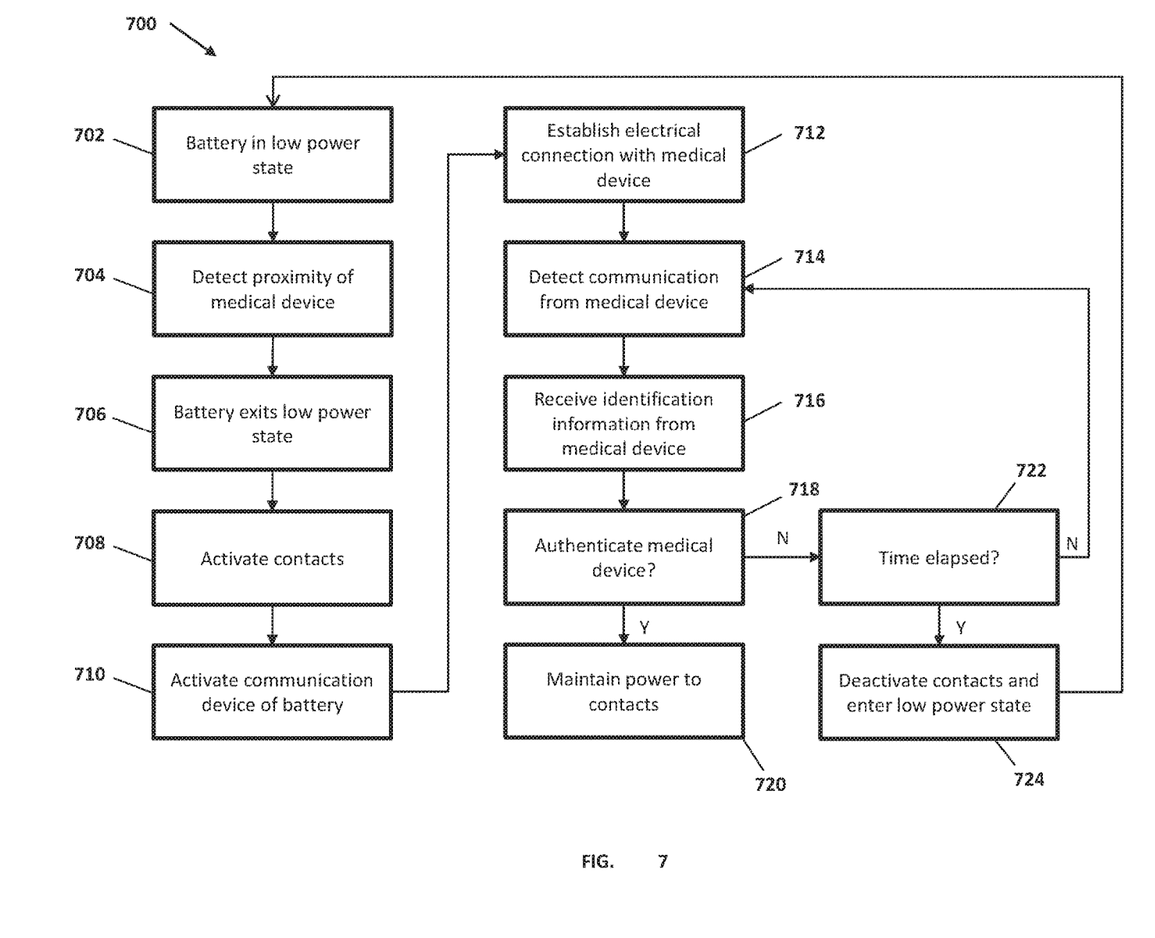
FIG. 7 is a flowchart of an example method of providing power to a medical device.

FIG. 7 is a flowchart of an example embodiment of a method 700 of providing power to a surgical tool or other medical device, such as tool 50 (shown in FIG. 2). As shown in FIG. 7, method 700 includes steps 702-724. One or more of the steps 702-724 of method 700 may be embodied as computer-executable instructions stored in a memory of battery 30 or tool 50 and may be executed by a processor or controller, such as processor 62 of tool 50 or by controller 400 of battery 30. While method 700 is described with reference to tool 50, it should be recognized that method 700 may be used with any suitable medical device.

In the example embodiment of FIG. 7, during step 702, when the medical device is separated from battery 30, battery 30 is in a low power state and cathode contact 78 and anode contact 80 are inactive (i.e., the cathode contact 78 and anode contact 80 are not able to provide current to the medical device). The low power state may be characterized as a power state in which at least some portions of controller 400 are disabled and controller 400 draws a current of about 20 milliamps (mA) or lower. Furthermore, at least some other components of battery 30 may be disabled in addition to the contacts 78 and 80, such as communication device 624. Alternatively, the low power state may be characterized as a power state in which at least some components of battery 30 are disabled, and portions of controller 400 are disabled such that controller 400 draws a current that is less than 5% of the current that controller 400 draws when the battery is in the high power state.

Also shown in FIG. 7, during step 704, the medical device is brought into proximity with battery 30 and battery 30 detects the proximity of the medical device. For example, in one such embodiment, the proximity sensor 622 of battery 30 may sense if either contact 78 or contact 80 are electrically connected to the medical device. However, in another embodiment, the proximity sensor 622 of battery 30 may sense the proximity wirelessly instead of sensing if either contact 78 or contact 80 are electrically connected to the medical device. For example, proximity sensor 622 of battery 30 may sense the presence of the magnet 64 or another suitable component or portion of the medical device. In response, proximity sensor 622 may output a proximity signal that has an amplitude that is proportional to, or otherwise based on, the proximity of the medical device to battery 30. Additionally, it should be recognized that proximity sensor 622 may be configured to sense the proximity in response to any suitable field, such as magnetic field, or a radio frequency signal generated by the medical device and received by battery 30.

During step 706, battery controller 400 receives the proximity signal and battery controller 400 "wakes up" by activating portions of controller 400 that were disabled during the low power state. Battery controller 400 then causes battery 30 to exit the low power state and enter the high power state. In one embodiment, controller 400 causes battery 30 to exit the low power state and enter the high power state if the amplitude of the proximity signal is greater than, or equal to, a predetermined proximity threshold value.

During step 708, controller 400 then activates cathode contact 78 and anode contact 80 (i.e., current is sourced through contacts 78 and 80 such that contacts 78 and 80 are able to provide current to the medical device). For example, in one embodiment, controller 400 transmits a signal to gating device 626 to cause gating device 626 to activate, thus enabling cells 32 to be electrically coupled to cathode contact 78 and anode contact 80. By coupling cells 32 to contacts 78 and 80, contacts 78 and 80 are activated and a current is sourced through the contacts 78 and 80.

As previously stated, contacts 78 and 80 are exposed and are therefore susceptible to corrosion when activated and exposed to liquids. Therefore, it should be noted that, by activating contacts 78 and 80 based on the proximity signal, the controller 400 aids in eliminating corrosion of the contacts 78 and 80. For example, in embodiments where the proximity is based on an electrical connection of the medical device to either contact 78 or 80, the controller 400 does not activate either contact 78 or 80 until contact 78 or 80 is electrically connected to the medical device. In embodiments where the proximity is sensed wirelessly, the controller 400 does not activate either contact 78 or 80 until sensor 622 senses the suitable magnetic field or a radio frequency signal generated by the medical device. As such, by ensuring a proximity between the battery 30 and the medical device before activating contacts 78 and/or 80, the controller 400 eliminates corrosion of contacts 78 and 80 by reducing a risk of contacts 78 and 80 being activated in undesirable circumstances, such as when contacts 78 and 80 are exposed to liquids.

During step 710, controller 400 activates battery communication device 624 by transmitting a signal to battery communication device 624, for example. Alternatively, battery communication device 624 may automatically be activated when controller 400 exits the low power state and enters the high power state. When battery communication device 624 is activated, battery communication device 624 may periodically attempt to communicate with tool communication device 602 as described more fully herein.

During step 712, battery 30 is brought into engagement with the medical device and cathode contact 78 and anode contact 80 are activated (i.e., when the battery is in the high power state), establishing an electrical connection between battery 30 and the medical device. As a result, power is provided from battery 30 to the medical device through contacts 78 and 80. Internal components of the medical device, including communication device 602, may then be activated. In response to the activation of communication device 602, communication device 602 may begin communicating with battery 30. For example, communication device 602 may begin transmitting authentication data to battery 30 (i.e., to battery communication device 624) to facilitate authenticating the medical device and/or battery 30. The authentication data may include, for example, identification information for the medical device as described above.

During step 714, controller 400 detects the communication from tool communication device 602 via battery communication device 624. In the embodiment of FIG. 7, battery communication device 624 receives the identification information from the medical device and transmits the identification information to controller 400 during step 716.

During step 718, controller 400 receives the identification information from battery communication device 624 and uses the identification information to authenticate the medical device. For example, controller 400 may reference a look-up table or another list of reference identifiers stored in memory and may compare the received identifier with the reference identifiers. If the received identifier matches one of the reference identifiers, controller 400 may determine that the medical device is compatible or approved for use with battery 30 and accordingly authenticates the medical device. If the medical device is authenticated, the battery controller 400 maintains power to contacts 78 and 80 during step 720 (i.e., continues to activate cathode contact 78 and anode contact 80) until the medical device is disconnected from battery 30.

However, if controller 400 does not authenticate the medical device (e.g., if the medical device identification information does not match any corresponding reference identifier), controller 400 continues monitoring communications from the medical device to determine whether any later-received identification information matches a reference identifier. During step 722, if a predetermined amount of time has elapsed after anode contact 80 has been activated without controller 400 authenticating the medical device, controller 400 deactivates cathode contact 78 and anode contact 80 by transmitting a signal to gating device 626 during step 724, thus disconnecting cells 32 from contacts 78 and 80. Battery 30 then returns to the low power state in step 702 as described above.

While the foregoing description relates to battery 30 authenticating a medical device based on identification information transmitted by the medical device, it should be recognized that the medical device may additionally or alternatively authenticate battery 30 based on identification information transmitted by battery 30 to the medical device in a similar manner. For example, the processor of the medical device (e.g., tool processor 62) may compare the identification information transmitted by battery 30 to a list of reference identifiers stored in a memory of the medical device. If the medical device processor determines that the identifiers match, the medical device may authenticate battery 30. The medical device may then transmit an authentication confirmation signal (using communication device 602) to battery 30 to indicate that the authentication of battery 30 was successful. In response to receiving the authentication confirmation signal, battery 30 may continue to activate contacts 78 and 80 in a similar manner as described above. Conversely, if battery 30 does not receive the authentication confirmation signal from the medical device within the predetermined amount of time, battery controller 400 may deactivate cathode contact 78 and anode contact 80 and cause battery 30 to enter a low power state.

It should be noted that in embodiments where the tool communication device 602 and the battery communication device 624 communicate bi-directionally, the tool communication device 602 may authenticate the battery 30 and the battery communication device 624 authenticates the medical device. In such an embodiment, battery communication device 624 receives identification information from the medical device and the tool communication device 602 receives identification information from the battery 30. As such, the controller 400 authenticates the medical device based on the identification information received from the medical device and the tool processor 62 authenticates the battery 30 based on the identification information received from the battery.

As previously stated, the data contact 82 may be used to communicate authentication data bi-directionally between the tool communication device 602 and the battery communication device 624. Also previously stated, in embodiments where the battery 30 does not include the data contact 82, the authentication data may be communicated bi-directionally between the tool communication device 602 and the battery communication device 624 using a suitable wireless protocol.

It should be noted that, because the authentication data and/or any other suitable data may be wirelessly communicated between the tool communication device 602 and the battery communication device 624, the battery 30 may optionally omit the data contact 82. In this way, the battery 30 may include fewer contacts which are susceptible to corrosion, while still being able to execute the method 700 of providing power to a surgical tool or other medical device.

A method of authenticating at least one of a battery and a medical device, the method comprising providing a battery including a battery controller and a contact, providing a medical device configured to couple to the contact, sensing a proximity of the medical device to the battery, and activating the contact in response to the proximity of the medical device to the battery.

A system comprising a medical device and a battery removably coupleable to the medical device, the battery comprising a cell for storing an electrical charge; a housing; a first contact; a second contact in selective communication with the cell, wherein the second contact is inactive when the battery is not in proximity to the medical device; a sensor configured to generate a proximity signal in response to a proximity of the medical device to the battery, wherein the proximity is not based on an electrical connection of the medical device to the first contact or the second contact; and a battery controller configured to receive the proximity signal and in response to receiving the proximity signal, cause the second contact to be activated. In some embodiments, the sensor comprises a Hall effect sensor and the medical device comprises a magnet.

A battery removably coupleable to a medical device, the battery comprising a cell for storing an electrical charge; a housing; a first contact; a second contact in selective communication with the cell, wherein the second contact is inactive when the battery is not in proximity to the medical device; a sensor configured to generate a proximity signal in response to the medical device and the battery being within a proximity of one another; a wireless communication device; and a battery controller configured to receive the proximity signal and cause the second contact to be activated in response to receiving the proximity signal, such that when the medical device is coupled to the battery and the second contact is activated, the wireless communication device receives an authentication signal to enable authentication.

A battery removably coupleable to a medical device, the battery comprising a cell for storing an electrical charge; a housing; a first contact; a second contact in selective communication with the cell, wherein the second contact is inactive when the battery is not in proximity to the medical device; a sensor configured to generate a proximity signal in response to the medical device and the battery being within a proximity of one another; a wireless communication device; and a battery controller configured to receive the proximity signal and cause the second contact to be activated in response to receiving the proximity signal, such that when the medical device is coupled to the battery and the second contact is activated, the wireless communication device transmits an authentication signal to enable authentication.

A system comprising a medical device comprising a first wireless communication device and a battery removably coupleable to the medical device, the battery comprising a cell for storing an electrical charge; a housing; a first contact; a second contact in selective communication with the cell, wherein the second contact is inactive when the battery is not in proximity to the medical device; a sensor configured to generate a proximity signal in response to the medical device and the battery being within a proximity of one another; a second wireless communication device; and a battery controller configured to receive the proximity signal and cause the second contact to be activated in response to receiving the proximity signal, such that when the medical device is coupled to the battery and the second contact is activated, one of the first and second wireless communication device transmits an authentication signal to the other of the first and second wireless communication device to enable authentication.

Although specific features of various embodiments of the disclosure may be shown in some drawings and not in others, this is for convenience only. In accordance with the principles of the disclosure, any feature of a drawing or other embodiment may be referenced and/or claimed in combination with any feature of any other drawing or embodiment.

This written description uses examples to describe embodiments of the disclosure and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:
   a medical device comprising a first wireless communication device; and
   a battery removably coupleable to the medical device, the battery comprising:
      a cell for storing an electrical charge;
      a housing;
      a first contact;
      a second contact in selective communication with the cell, wherein the second contact is inactive when the battery is not in proximity to the medical device;
      a sensor disposed within the housing and being configured to generate a proximity signal in response to the medical device and the battery being within a proximity of one another;
      a second wireless communication device; and
      a battery controller configured to:
         receive the proximity signal; and
         cause the second contact to be activated in response to receiving the proximity signal, such that when the medical device is coupled to the battery and the second contact is activated, the first wireless communication device transmits an authentication signal to the second wireless communication device to enable authentication.

2. The system of claim 1, wherein the first wireless communication device comprises an RF transceiver and the second wireless communication device comprises an RF transceiver.

3. The system of claim 1, wherein the first and second wireless communication devices comprise a wireless communication device configured to transmit a wireless authentication signal to the other of the first and second wireless communication device to enable authentication such that the proximity is not based on an electrical connection of the medical device to the first contact or the second contact.

4. The system of claim 1, wherein the sensor comprises a Hall effect sensor and the medical device comprises a magnet configured to generate a magnetic field and positioned such that the Hall effect sensor senses the magnetic field when the medical device and the battery are within the proximity of one another.

5. The system of claim 4, wherein the sensor is configured to generate the proximity signal in response to the Hall effect sensor sensing the magnetic field of the magnet.

6. The system of claim 1, wherein the sensor is configured to generate the proximity signal in response to the sensor sensing a radio frequency signal from the medical device.

7. The system of claim 1, wherein the authentication signal includes identification information of the medical device.

8. The system of claim 1, wherein the second wireless communication device of the battery is configured to:
   receive the authentication signal from the first wireless communication device of the medical device; and
   authenticate the medical device in response to receiving the authentication signal.

9. The system of claim 1, wherein the first wireless communication device of the medical device is configured to:
   receive the authentication signal from the second wireless communication device of the battery; and
   authenticate the battery in response to receiving the authentication signal.

10. The system of claim 1, wherein the first and second wireless communication devices are configured to:
    establish bi-directional communication with each other; and
    transmit the authentication signal to the other of the first and second wireless communication device such that the first wireless communication device is configured to authenticate the battery in response to receiving the authentication signal from the second wireless communication device and the second wireless communication device is configured to authenticate the medical device in response to receiving the authentication signal from the first wireless communication device.

11. The system of claim 1, wherein the second contact remains activated in response to authenticating the medical device.

12. The system of claim 1, wherein the battery controller is configured to:

determine whether the medical device has not been authenticated within a predetermined amount of time after the second contact has been activated; and deactivate the second contact if the medical device has not been authenticated within the predetermined amount of time after the second contact has been activated.

13. The system of claim 1, wherein the battery is in a low power state before the second contact is activated, wherein the battery is in a high power state after the second contact is activated, and wherein the battery controller causes the battery to exit the low power state and enter the high power state in response to the proximity signal.

14. The system of claim 13, wherein the battery controller is configured to:

determine whether the medical device has been authenticated within a predetermined amount of time after the second contact has been activated; and cause the battery to enter the low power state if the medical device has not been authenticated within the predetermined amount of time.

15. A method of authenticating at least one of a battery and a medical device, the method comprising steps of:

providing a battery comprising a battery controller, a contact, and a first wireless communication device;

providing a medical device comprising a second wireless communication device and being configured to couple to the contact;

sensing a proximity of the medical device to the battery;

wirelessly transmitting an authentication signal between the first and second wireless communication devices in response to proximity; and activating the contact in response to the proximity of the medical device to the battery.

16. The method of claim 15, wherein the step of sensing a proximity of the medical device to the battery is not based on an electrical connection between the medical device and the battery.

17. The method of claim 15, wherein the step of sensing a proximity of the medical device to the battery comprises a step of generating a proximity signal in response to sensing at least one of a magnetic field and a radio frequency signal from the medical device.

18. The method of claim 15, further comprising a step of operating the battery in a low power state before the contact is activated and a step of operating the battery in a high power state after the contact is activated.

19. The method of claim 18, further comprising steps of:

determining whether the medical device has not been authenticated within a predetermined amount of time after the contact has been activated; and deactivating the contact such that the battery enters the low power state if the medical device has not been authenticated with the predetermined amount of time after the contact has been activated.

20. A system comprising:

a medical device; and a battery removably coupleable to the medical device, the battery comprising:

cell for storing an electrical charge;

a housing;

a first contact;

a second contact in selective communication with the cell, wherein the second contact is inactive when the battery is not in proximity to the medical device;

a sensor configured to generate a proximity signal in response to a proximity of the medical device to the battery, wherein the proximity is not based on an electrical connection of the medical device to the first contact or the second contact;

a battery controller configured to:

receive the proximity signal;

in response to receiving the proximity signal, cause the second contact to be activated, wherein one of the medical device and the battery comprises a communication device, and wherein, when the medical device is coupled to the battery and the second contact is activated, one of the medical device and the battery uses the communication device to transmit an authentication signal to the other of the battery and medical device to enable authentication.

* * * * *

UNITED STATES PATENT AND TRADEMARK OFFICE
CERTIFICATE OF CORRECTION

PATENT NO. : 10,425,894 B2
APPLICATION NO. : 16/009637
DATED : September 24, 2019
INVENTOR(S) : Conner Bacon Howell et al.

It is certified that error appears in the above-identified patent and that said Letters Patent is hereby corrected as shown below:

In the Claims

Column 20, Line 17, in Claim 20:
Please replace "cell for storing an electrical charge;" with --a cell for storing an electrical charge;--

Signed and Sealed this
Twenty-fourth Day of March, 2020

Andrei Iancu
*Director of the United States Patent and Trademark Office*